United States Patent
Oakley et al.

(10) Patent No.: US 8,945,013 B2
(45) Date of Patent: Feb. 3, 2015

(54) REAL TIME ULTRASOUND PROBE

(75) Inventors: Clyde G. Oakley, Centennial, CO (US);
John J Squires, Elkton, MD (US);
Joshua J Wardell, Littleton, CO (US);
Fred L Hatcher, Parker, CO (US);
Richard W. Denny, Castle Rock, CO (US); Johannes Haftmann, Heldeck (DE)

(73) Assignee: W. L. Gore & Associates, Inc., Newark, DE (US)

( * ) Notice: Subject to any disclaimer, the term of this patent is extended or adjusted under 35 U.S.C. 154(b) by 87 days.

(21) Appl. No.: 12/993,477

(22) PCT Filed: Jun. 1, 2009

(86) PCT No.: PCT/US2009/045861
§ 371 (c)(1),
(2), (4) Date: Jan. 21, 2011

(87) PCT Pub. No.: WO2009/146459
PCT Pub. Date: Dec. 3, 2009

(65) Prior Publication Data
US 2011/0105907 A1 May 5, 2011

Related U.S. Application Data

(63) Continuation-in-part of application No. 12/130,356, filed on May 30, 2008, now Pat. No. 8,506,490.

(51) Int. Cl.
*A61B 8/14* (2006.01)
*G10K 11/35* (2006.01)

(52) U.S. Cl.
CPC .................................... *G10K 11/355* (2013.01)

USPC ........... 600/459; 600/446; 600/445; 600/444; 600/437; 367/171

(58) Field of Classification Search
None
See application file for complete search history.

(56) References Cited

U.S. PATENT DOCUMENTS

| | | | |
|---|---|---|---|
| 3,955,561 A | 5/1976 | Eggleton | |
| 4,092,867 A | 6/1978 | Matzuk | |
| 4,149,419 A | 4/1979 | Connell, Jr. et al. | |
| 4,185,501 A | 1/1980 | Proudian et al. | |
| 4,316,271 A * | 2/1982 | Evert | 367/140 |

(Continued)

FOREIGN PATENT DOCUMENTS

| | | |
|---|---|---|
| EP | 0 982 711 | 1/2000 |
| EP | 1535574 | 6/2005 |

(Continued)

*Primary Examiner* — Nicholas Evoy
(74) *Attorney, Agent, or Firm* — Amy L. Miller

(57) ABSTRACT

An external ultrasound probe assembly capable of scanning a three-dimensional volume is provided. The ultrasound probe assembly contains a plurality of ultrasonic transducers disposed along a longitudinal axis of the probe assembly. The plurality of ultrasonic transducers is disposed on a mechanism operable to reciprocally pivot the plurality of ultrasonic transducers enabling the plurality of ultrasonic transducers to scan the entire three-dimensional volume. A helically disposed electrical interconnection member may be disposed about a pivot axis of the plurality of ultrasonic transducers and may electrically interconnect the plurality of ultrasonic transducers to an ultrasound imaging system. The ultrasound probe assembly may be fluid filled and contain bubble position control and fluid expansion compensation features.

22 Claims, 9 Drawing Sheets

(56) References Cited

U.S. PATENT DOCUMENTS

| | | | |
|---|---|---|---|
| 4,398,425 A | 8/1983 | Matzuk | |
| 4,399,703 A | 8/1983 | Matzuk | |
| 4,421,118 A * | 12/1983 | Dow et al. | 600/446 |
| 4,455,872 A * | 6/1984 | Kossoff et al. | 73/618 |
| 4,474,184 A * | 10/1984 | Harui | 600/459 |
| 4,567,895 A * | 2/1986 | Putzke | 600/445 |
| 4,747,411 A * | 5/1988 | Ledley | 600/443 |
| 4,756,313 A * | 7/1988 | Terwilliger | 600/462 |
| 4,757,818 A * | 7/1988 | Angelsen | 600/446 |
| 4,784,148 A * | 11/1988 | Dow et al. | 600/446 |
| 4,794,930 A | 1/1989 | Machida et al. | |
| 4,841,979 A | 6/1989 | Dow et al. | |
| 4,895,158 A | 1/1990 | Kawabuchi et al. | |
| 4,913,155 A | 4/1990 | Dow et al. | |
| 4,977,898 A | 12/1990 | Schwarzschild et al. | |
| 5,070,879 A | 12/1991 | Herres | |
| 5,088,495 A * | 2/1992 | Miyagawa | 600/446 |
| 5,152,294 A * | 10/1992 | Mochizuki et al. | 600/459 |
| 5,159,931 A | 11/1992 | Pini | |
| 5,176,142 A * | 1/1993 | Mason | 600/463 |
| 5,226,422 A | 7/1993 | McKeighen et al. | |
| 5,351,692 A | 10/1994 | Dow et al. | |
| 5,379,772 A | 1/1995 | Imran | |
| 5,402,789 A * | 4/1995 | Dow et al. | 600/446 |
| 5,460,179 A * | 10/1995 | Okunuki et al. | 600/444 |
| 5,486,162 A * | 1/1996 | Brumbach | 604/22 |
| 5,531,119 A * | 7/1996 | Meyers | 73/661 |
| 5,662,116 A | 9/1997 | Kondo et al. | |
| 5,678,551 A | 10/1997 | Stevens | |
| 5,762,066 A * | 6/1998 | Law et al. | 600/439 |
| 5,842,473 A | 12/1998 | Fenster et al. | |
| 6,126,606 A * | 10/2000 | Bergstoel | 600/459 |
| 6,152,144 A * | 11/2000 | Lesh et al. | 128/898 |
| 6,461,298 B1 | 10/2002 | Fenster et al. | |
| 7,494,469 B2 * | 2/2009 | Bruestle | 600/459 |
| 7,734,324 B2 * | 6/2010 | Biglieri et al. | 600/407 |
| 7,972,272 B2 * | 7/2011 | Munce et al. | 600/462 |
| 8,214,010 B2 * | 7/2012 | Courtney et al. | 600/407 |
| 8,460,195 B2 * | 6/2013 | Courtney et al. | 600/463 |
| 8,506,490 B2 * | 8/2013 | Haftmann et al. | 600/459 |
| 8,535,232 B2 * | 9/2013 | Dietz et al. | 600/466 |
| 8,585,601 B2 * | 11/2013 | Sverdlik et al. | 600/459 |
| 8,611,189 B2 * | 12/2013 | Vaezy et al. | 367/152 |
| 8,636,664 B2 * | 1/2014 | Brannan | 600/439 |
| 2004/0122319 A1 | 6/2004 | Mehi et al. | |
| 2005/0124889 A1 * | 6/2005 | Flesch | 600/445 |
| 2005/0240102 A1 | 10/2005 | Rachlin et al. | |
| 2006/0191344 A1 * | 8/2006 | Hashimoto | 73/632 |
| 2006/0270935 A1 * | 11/2006 | Ariff et al. | 600/437 |
| 2007/0167813 A1 | 7/2007 | Lee et al. | |
| 2007/0220977 A1 * | 9/2007 | Hart et al. | 73/632 |
| 2008/0015444 A1 * | 1/2008 | Cho | 600/459 |
| 2008/0021317 A1 | 1/2008 | Sumanaweera | |
| 2008/0097403 A1 * | 4/2008 | Donaldson et al. | 604/528 |
| 2008/0287797 A1 | 11/2008 | Lee et al. | |
| 2009/0247879 A1 * | 10/2009 | Angelsen et al. | 600/463 |
| 2009/0299193 A1 * | 12/2009 | Haftman et al. | 600/459 |
| 2009/0318813 A1 * | 12/2009 | Thompson et al. | 600/459 |
| 2010/0036258 A1 * | 2/2010 | Dietz et al. | 600/466 |
| 2010/0234734 A1 * | 9/2010 | Cho | 600/459 |
| 2010/0280316 A1 * | 11/2010 | Dietz et al. | 600/109 |
| 2012/0197113 A1 * | 8/2012 | Courtney et al. | 600/427 |

FOREIGN PATENT DOCUMENTS

| | | |
|---|---|---|
| JP | 59-124355 | 8/1984 |
| JP | S59124357 | 8/1984 |
| JP | 64-027538 | 1/1989 |
| JP | H114825 | 1/1999 |
| JP | 2004-089532 | 3/2004 |

* cited by examiner

REAL TIME ULTRASOUND PROBE

BACKGROUND

Ultrasound imaging probes continue to enjoy widespread use in the medical field. Ultrasound probes are used in a wide variety of applications where it is desired to non-invasively generate images of the internal structure of a patient. Additionally, ultrasound probes are utilized for a wide variety of laparoscopic, endoscopic and intravascular imaging applications. The ultrasound images provided by imaging probes may, for example, be used for diagnostic purposes.

Ultrasound imaging probes typically include a plurality of parallel piezoelectric transducer elements arranged along a longitudinal axis, with each element interconnected to a pair of electrodes. By sequentially sending and receiving ultrasonic energy from each transducer element, the ultrasound imaging probe is operable to scan an imaging plane along the length of, and perpendicular to, the plurality of parallel piezoelectric transducer elements.

Ultrasound imaging probes capable of scanning three dimensions have been developed that scan a three-dimensional volume by reciprocally pivoting the plurality transducer elements arranged along the longitudinal axis, thus sweeping the imaging plane through a three-dimensional volume.

SUMMARY

As the applications for, and use of, ultrasound imaging probes capable of scanning three dimensions continue to expand, so does the need for ultrasound probe designs that yield higher imaging performance, greater miniaturization, greater robustness and/or increased production efficiencies. In this regard, the ability to realize enhanced performance, miniaturization, robustness and production efficiencies related to ultrasound imaging probes through improvements to component configuration, fluid pressure management, shock absorption capability, bubble management and array electrical interconnections used in ultrasound imaging probes becomes particularly significant.

In view of the foregoing, an object of embodiments described herein may be to provide improved component configurations to yield, inter alia, greater overall compactness and reduced weight. An additional objective may be to provide improved fluid pressure management capability. A further objective may be to provide enhanced shock absorption capabilities from shocks that, for example, may occur when the imaging probe is dropped. Another objective may be to improve the management of bubbles that may form or enter into a fluid-filled portion of the imaging probe such that the bubbles do not substantially interfere with imaging performance. A further objective may be to provide improved electrical interconnection members between the moving components of the imaging probe (e.g., a transducer array) and the static components of the imaging probe (e.g., the outer case).

One or more of the above-noted objectives and additional advantages may be realized by the ultrasound probe comprising the present invention. The inventive probe includes a case having an enclosed volume, a fluid disposed within the enclosed volume and an ultrasound transducer array disposed within the enclosed volume. The fluid may fill the enclosed volume, wherein the ultrasound transducer array is immersed within the fluid to facilitate enhanced acoustic coupling upon bodily contact of the probe during imaging procedures. In certain embodiments the ultrasound transducer array may be disposed for reciprocal pivotal movement through the fluid within the probe case, thereby yielding real-time, three-dimensional images of internal body tissue. Such an arrangement may be configured for external, relative to a patient, use in imaging an internal volume of the patient. Such an arrangement may be configured for hand-held use where a technician or other operator may hold the probe in a hand while manipulating the probe relative to an internal volume of the patient.

In one aspect, the ultrasound probe may include a bellows member having a flexible, closed-end portion located within the fluid in the case and an open-end isolated from the fluid, wherein the bellows member is collapsible and expansible in response to volumetric variations in the fluid. As may be appreciated, the provision of a bellows member may maintain operational integrity of the ultrasound probe when exposed to conditions that may cause a volumetric change in the contained fluid.

In one approach, the case of the ultrasound probe may include a proximal chamber located adjacent to and sealably separated from the enclosed volume, wherein the open end of the bellows member is in open communication with the proximal chamber for internal pressure equalization therebetween. The provision of a proximal chamber facilitates pressure equalization and offers protection in relation to the open end of the bellows member.

In conjunction with this approach, the case may include a first portion defining the enclosed volume and a second portion that is selectively disconnectable from and connectable to the first portion to define the proximal chamber. The provision of selectively connectable and disconnectable portions facilitates ready access to the open end of the bellows during initial assembly as well as subsequent servicing. Relatedly, the ultrasound probe may further include a sealable port extending through a proximal wall of the first portion of the case, wherein the sealable port may be accessed upon disconnection of the second portion from the first portion for selectively passing fluid into or removing fluid from the enclosed volume.

At least the closed end portion of the bellows member may be elastically deformable. In this regard, the closed end portion of the bellows member may be elastically expandable in response to volumetric variations in the fluid. The bellows member may be operable to maintain operational integrity of the ultrasound probe despite fluid volume changes that may occur due to exposure of the ultrasound probe to relatively warm or cool temperatures during, for example, transport and/or storage. Such an elastically expandable bellows member may be particularly advantageous with respect to low temperatures where the fluid typically contracts more than the case.

In another aspect, the ultrasound probe may include a bubble-trap member fixedly positioned relative to the case within the enclosed volume. The bubble-trap member may have a distal-facing concave surface, wherein a distal portion of the enclosed volume is defined distal to the bubble-trap member and a proximal portion of the enclosed volume is defined proximal to the bubble-trap member. The ultrasound transducer array may be located in the distal portion and an aperture may be provided through the bubble-trap member to fluidly connect the distal portion of the enclosed volume to the proximal portion of the enclosed volume. As may be appreciated, bubbles present in the contained fluid can negatively affect images obtained by the ultrasound transducer array and are undesired. In the described arrangement, the probe may be oriented with the proximal end upwards, wherein bubbles may be directed by the concave surface through the aperture of the bubble-trap, and effectively isolated from the ultrasound transducer array by virtue of the bubbles being trapped in the proximal portion of the enclosed volume by the bubble-trap.

In one embodiment, the ultrasound transducer array and the bubble-trap member may each be supportably cantilevered from an end of the enclosed volume that is proximal to the bubble-trap member, wherein the bubble-trap member and the ultrasound transducer array are otherwise free from engagement with the case (e.g., free from contact with sidewalls of the cases). The proximal, cantilevered support of the bubble-trap member and ultrasound transducer array facilitates probe compactness and yields enhanced durability. In the later regard, increased impact resistance may be realized.

In another embodiment, a peripheral rim of the bubble-trap member may be spaced a predetermined distance from the case such that any bubble(s) within the fluid are restricted from passing between the peripheral rim of the bubble-trap and the case. In an arrangement, a gasket member may be disposed between the peripheral rim of the bubble trap and the case. The gasket member may restrict passage of bubbles within the fluid between the peripheral rim and the case. The gasket member may be fixedly interconnected to the peripheral rim or the case. The gasket member may be slidable relative to the other one of the peripheral rim and the case upon relative movement therebetween. The gasket member may be lubricious and compressible and may conform to the region between the peripheral rim and the case. The gasket member may include expanded polytetrafluoroethylene (ePTFE). A resilient member may be interposed between a cantilevered end of the bubble trap and the case. The resilient member may be compressible to permit a predetermined amount of relative movement between the bubble trap and case. The predetermined amount of relative movement permitted by the resilient member may correspond to a degree of relative movement permitted by the gasket member.

In yet another embodiment, the ultrasound transducer array may be supportably interconnected to the bubble-trap member (e.g., interconnected to a distal-facing surface thereof) within the distal portion of the enclosed volume. By way of example, at least a first support member may be fixedly interconnected to the bubble-trap member, and an axle may be fixedly supported by the support member, wherein the axle defines a pivot axis within the enclosed volume. In turn, the ultrasound transducer array may be pivotably supported by the axle for pivotal movement about the pivot axis. In this regard, at least one bearing member may be rotatably mounted to the axle, wherein the ultrasound transducer array is fixedly interconnected to the bearing member for co-rotation therewith about the pivot axis.

In one implementation, a first support member and a second support member may be fixedly interconnected to the bubble-trap member within the enclosed volume (e.g., in symmetric locations relative to a probe center axis), wherein an axle is fixedly supported by and between the first support member and the second support member. In turn, first and second bearing members may be rotatably mounted to the first and second support members, respectively, wherein each of the bearing members are fixedly interconnected to the ultrasound transducer array for co-rotation therewith about the pivot axis.

In an additional embodiment, a distal-facing concave surface of the bubble-trap member may define a recess. In turn, the probe may include a motor at least partially disposed, or nested, within the recess of the bubble-trap member, wherein the motor is operatively interconnected to the ultrasound transducer array to effect reciprocal pivotal movement thereof. Such an arrangement enhances probe compactness.

By way of example, the motor may drive an output wheel oriented substantially perpendicular to a pivot axis about which the ultrasound transducer array is pivotably supported for reciprocal movement. In turn, a timing belt may be disposed for driven movement by the output wheel so as to rotate one or more bearing members back and forth about the pivot axis, wherein the interconnected ultrasound transducer array may be reciprocally pivoted for dynamic imaging.

In an arrangement, a filter may be disposed across the aperture. The filter may be configured such that air may pass through the aperture while the fluid may be unable to pass through the aperture. The filter may include ePTFE.

In a further aspect, the ultrasound transducer array may be disposed for reciprocal movement about a pivot axis within the enclosed volume and the ultrasound probe may include an electrical interconnection member having a first portion disposed within the enclosed volume and helically disposed about the pivot axis and interconnected to the ultrasound transducer array. Upon the reciprocal pivotal movement, the helically disposed first portion of the first electrical interconnection member may tighten and loosen about the pivot axis. The first electrical interconnection member may be ribbon-shaped and include a plurality of conductors arranged side-by-side with electrically non-conductive material therebetween.

In another aspect, the ultrasound transducer array may be disposed for reciprocal movement within the enclosed volume. The ultrasound probe may include an electrical interconnection member having at least a portion helically disposed within the enclosed volume and fixedly interconnected to the ultrasound transducer array. Upon the reciprocal movement the helically disposed portion may loosen and tighten along a length thereof.

In an embodiment, the helically disposed portion may be disposed about a pivot axis of the ultrasound transducer array. In an arrangement, an entirety of the helically disposed portion may be offset from the pivot axis. In such an arrangement, no portion of the helically disposed portion of the electrical interconnection member may intersect with the pivot axis. In an embodiment, the electrical interconnection member may have at least a portion fixedly interconnected relative to the case. The electrical interconnection member may be ribbon-shaped and include a plurality of conductors arranged side-by-side with electrically non-conductive material therebetween.

In yet a further aspect, the ultrasound transducer array may be disposed for reciprocal movement about a pivot axis within the enclosed volume, and a shell member may be disposed about at least a portion of the pivot axis for co-pivotal movement with ultrasound transducer array within the enclosed volume. The shell member may be of a streamlined configuration to reduce drag forces encountered upon reciprocal movement of the ultrasound transducer array through the fluid. The probe may further include at least a first electrical interconnection member (e.g. for conveying ultrasound imaging signals to/from the ultrasound transducer array). The first electrical interconnection member may include a first portion coiled about the pivot axis and interconnected to the ultrasound transducer array within the shell member.

In one embodiment at least a first support member may be fixedly positioned relative to the case within the enclosed volume. In turn, an axle may be fixedly supported by the support member to define the pivot axis, wherein the ultrasound transducer array is rotatably interconnected to the axle, and wherein the first portion of the first electrical interconnection member is coiled about the axle. In this embodiment, the first electrical interconnection member may include a second portion adjoining the first portion, wherein the second portion is fixedly positioned relative to the case within the enclosed volume, and wherein upon reciprocal movement of the ultrasound transducer array, the coiled first portion of the first electrical interconnection member tightens and loosens about the axle. In this regard, the second portion of the first electrical interconnection member may be disposed to extend through a slot of the second shell member. The slot of the shell member is oriented transverse (e.g., orthogonal) to the pivot axis, wherein the slot reciprocates back and forth about the second portion of the first electrical interconnection member that extends therethrough.

In one approach, the first electrical interconnection member may be ribbon-shaped and may comprise a plurality of conductors arranged side-by-side with electrically non-conductive material disposed therebetween across the width of the member. By way of example, the first electrical interconnection member may comprise a GORE™ Microminiature Flat Cable available from WL Gore & Associates, Newark, Del., U.S.A, wherein the first portion of the first electrical interconnection member may be disposed so that a top or bottom side thereof faces and wraps about a pivot axis of an ultrasound transducer array.

In another embodiment, the first portion of the first electrical interconnection member may be coiled a plurality of times about the pivot axis. More particularly, the first portion of the first electrical interconnection member may be helically disposed about the pivot axis a plurality of times. In one approach, the first electrical interconnection member may be helically disposed about the pivot axis in a non-overlapping manner, i.e. where no portion of the first electrical interconnection member overlies another portion thereof. In such an embodiment, the first electrical interconnection member may be ribbon-shaped and may comprise a plurality of conductors arranged side-by-side with electrically non-conductive material disposed therebetween.

In yet a further embodiment, the ultrasound probe may include at least a second electrical interconnection member having a first portion coiled about the pivot axis and interconnected to the ultrasound transducer array within the shell member. In this regard, each of the first electrical interconnection member and second electrical interconnection member may be ribbon-shaped and comprise a plurality of conductors arranged side-by-side with electrically non-conductive material therebetween. In one approach, the coiled first portion of the second electrical interconnection member may overlie at least a portion of the coiled first portion of the first electrical interconnection member. By way of example, the first portions of the first and second electrical interconnection members may be helically disposed about the pivot axis a plurality of times.

In one implementation, each of the first and second electrical interconnection members may comprise second portions adjoining the corresponding first portions thereof, wherein each of the second portions are fixedly positioned relative to the case within the enclosed volume. In turn, upon reciprocal, pivotal movement of the ultrasound transducer array the coiled first portions of the first and second electrical interconnection members tighten and loosen about the pivot axis.

In yet a further aspect, the ultrasound transducer array may comprise an arcuate surface portion that conformally adjoins an arcuate surface portion of the shell member. In one approach, the arcuate surface portions of the ultrasound transducer array and the shell member may combinatively define an ellipsoid configuration. By way of example, the case may comprise a sonolucent distal portion having a configuration coincidental to the arcuate surface portion of the array, wherein a substantially constant spacing is maintained between the arcuate surface portion of the ultrasound transducer array and the distal portion of the case during reciprocal movement of the ultrasound transducer array about the pivot axis.

In an aspect, an external ultrasound probe imaging system is provided. The external ultrasound probe imaging system includes an imaging system, an external ultrasound probe disposed remotely from the imaging system, a cable interconnected to the imaging system and the external ultrasound probe, and a controller operable to provide control signals to a motor driver. The external ultrasound probe may include a case having an enclosed volume, a fluid disposed within the enclosed volume, an ultrasound transducer array disposed within the enclosed volume, a motor and a motor driver. The motor may be disposed within the enclosed volume and may be interconnected to the ultrasound transducer array to reciprocally pivot the ultrasound transducer array about a pivot axis. The motor driver may be disposed within the case to provide drive signals to the motor.

In an embodiment, the controller may be disposed within the imaging system. Such an embodiment may include a filter operatively disposed between the controller and the motor driver. The filter may be disposed within the imaging system.

The cable further may include a connector for connecting the cable to the imaging system. In an embodiment, the controller may be disposed within the connector. Such an embodiment may include a filter operatively disposed between the controller and the motor driver disposed within the connector.

In an embodiment, the controller may be disposed within the case. A filter may be disposed within the case and operatively disposed between the controller and the motor driver.

The driver may be operable to provide pulse width modulation (PWM) control signals to the motor.

In conjunction with the present invention, a number of inventive methods may be realized. For example, a method is provided for maintaining fluid pressure within a case of a probe having an ultrasound transducer array. The method may include locating a flexible bellows, wherein the flexible bellows includes a closed-end portion positioned in the fluid located within the case, and an open-end thereof positioned in an isolated location from the fluid. The method may include collapsing the bellows member in response to a volumetric expansion of the fluid. The method may include expanding the bellows member in response to a volumetric contraction of the fluid. In conjunction with such method, the open-end of the bellows may be disposed in open communication with a proximal chamber adjacent to and sealably separate from the enclosed volume. In turn, the method may include equalizing internal pressure within the bellows member and the proximal chamber of the ultrasound probe.

The various features discussed above in relation to each aforementioned aspect may be utilized by any of the aforementioned aspects. Additional aspects and corresponding advantages will be apparent to those skilled in the art upon consideration of the further description that follows.

DETAILED DESCRIPTION

Figure 1:
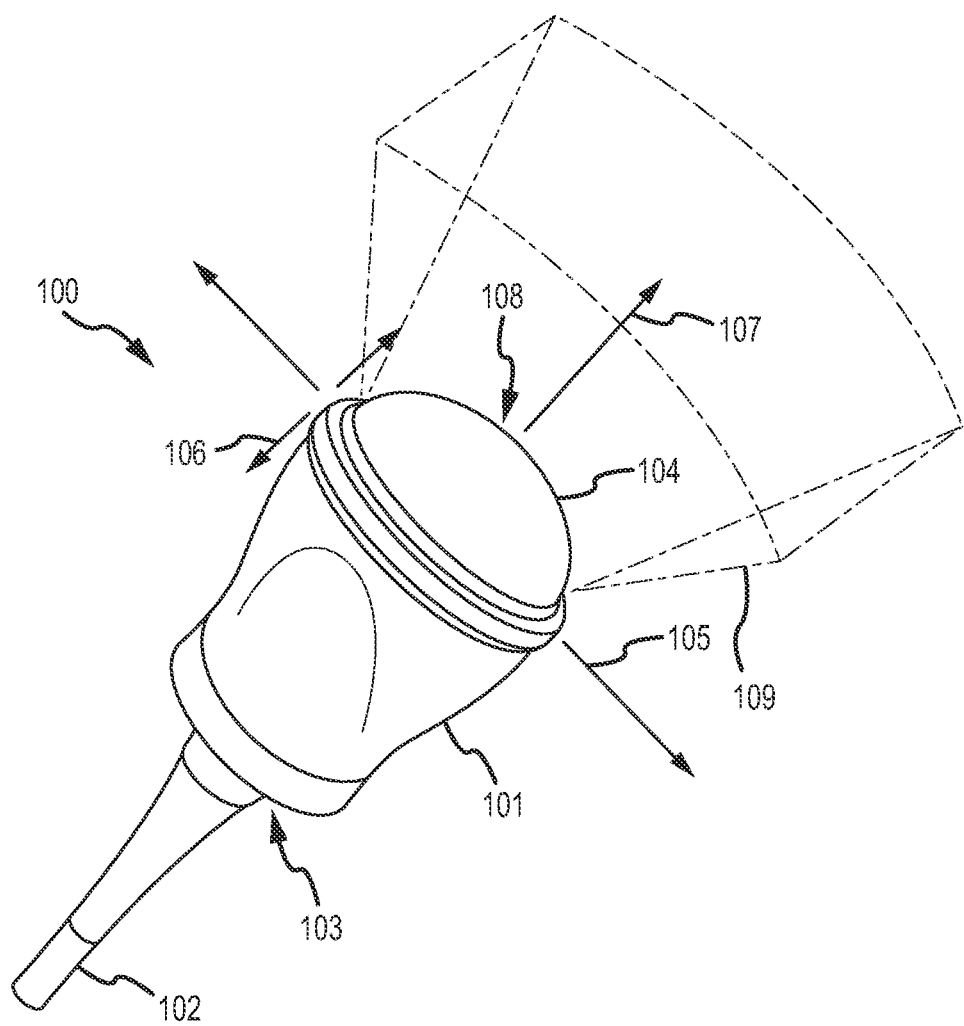
FIG. 1 illustrates an isometric view of an embodiment of an ultrasound probe assembly.

FIG. 1 illustrates a perspective view of an ultrasound transducer probe assembly 100. The ultrasound transducer probe assembly 100 may be an external device in that it may be sized and configured to be disposed external to a patient when used to image a volume within the patient. The probe assembly 100 includes a case 101. The case 101 may generally be sized and shaped for hand-held use by a technician or other operator. A cable 102 is interconnected to the probe assembly at a proximal end 103 of the probe assembly 100. The cable 102 operatively connects the probe assembly 100 to an ultrasound imaging apparatus (not shown). Generally, the probe assembly 100 includes a plurality of ultrasonic transducers (described below with reference to FIG. 4) contained within the case 101 and operable to transmit ultrasonic energy through a sonolucent distal portion 104 of the case 101. In the probe assembly 100, the sonolucent distal portion 104 is in the shape of a dome. The ultrasonic energy, in the form of acoustic waves, may be directed through the sonolucent distal portion 104 and through the outer surface of a patient and into the internal structure of the patient. The acoustic waves may interact with and reflect off of various internal features. These reflections may then be detected by the probe assembly 100 and displayed as images of the internal structure of the patient by the ultrasound imaging apparatus.

As shown in FIG. 1, the probe assembly 100 has a longitudinal axis 105 parallel with the width of the probe assembly 100 and an elevation axis 106 perpendicular to the longitudinal axis 105. The probe assembly also contains a central axis 107 extending along the length of the probe assembly 100 from the proximal end 103 to a distal end 108.

In general, the images generated by the probe assembly 100 may be of a subject (e.g., internal structure of a patient) within an image volume 109. The image volume 109 extends outwardly from the probe assembly 100 along the central axis 107. The entire image volume 109 may be scanned by the plurality of ultrasonic transducers contained within the case 101. The plurality of ultrasonic transducers may be disposed along the longitudinal axis 105 and may be operable to scan an image plane with a width along the longitudinal axis 105 and a depth perpendicular to the transducers. The plurality of ultrasonic transducers may be disposed on a mechanism operable to reciprocally pivot the plurality of ultrasonic transducers about the longitudinal axis 105 such that the image plane is swept about the longitudinal axis 105 along the elevation axis 106. The sweeping of the image plane about the longitudinal axis 105 enables the plurality of ultrasonic transducers to scan the entire image volume 109 and thus a three dimensional image of the image volume 109 may be generated. The probe assembly 100 may be operable to reciprocally pivot the plurality of ultrasonic transducers at a rate sufficient enough to generate real-time or near real-time three-dimensional images of the image volume 109. In this regard, the ultrasound imaging apparatus may be operable to display live or near-live video of the image volume. Commonly, imaging parameters within the image volume 109, for example focal length and depth of field, may be controlled through electronic means known to those skilled in the art.

Figure 2:
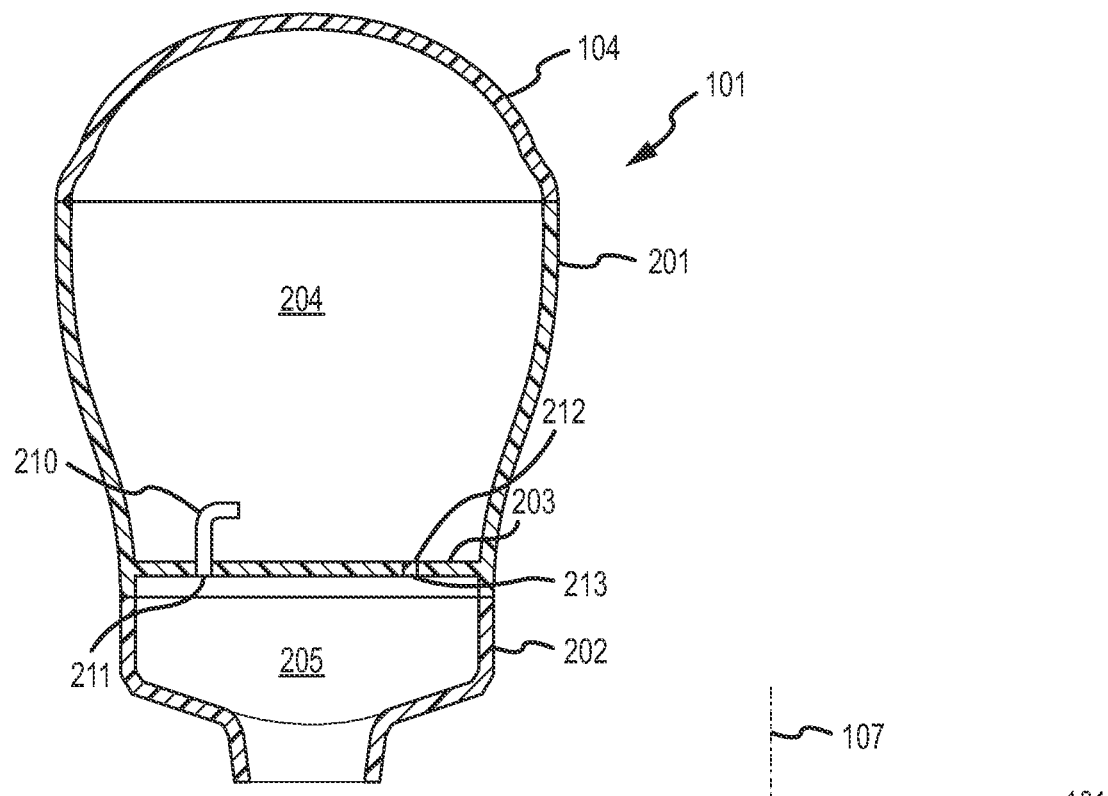
FIG. 2 is a partial cross-sectional view of selected components of the ultrasound probe assembly of FIG. 1.

FIG. 2 is a partial cross sectional view of a portion of the case 101 of the probe assembly 100 of FIG. 1. For explanatory purposes, several internal components of the probe assembly 100 are not shown in FIG. 2. The case 101 includes a main portion 201 disposed between the sonolucent distal portion 104 and a proximal portion 202 of the case 101. The main portion 201 may include a proximal wall in the form of a base member 203. Together the main portion 201, including the base member 203, and the sonolucent distal portion 104 may define an enclosed portion 204 therebetween. Additionally, a proximal portion of the main portion 201, the base member 203 and the proximal portion 202 may form a proximal chamber 205. As may be appreciated, the base member 203 separates the enclosed volume 204 from the proximal chamber 205.

The enclosed volume 204 may be fluid filled and sealed. The fluid may be an oil selected for its acoustical properties. In this regard, the enclosed volume 204 may be sealed such that the fluid within the enclosed volume 204 is substantially unable to leak out of the enclosed volume 204. Furthermore, the enclosed volume 204 may be sealed to substantially prevent gasses (e.g., air) from entering into the enclosed volume 204.

The proximal chamber 205 may be sealably separated from the enclosed volume 204. The proximal portion 202 may be selectably disconnectable from and selectably connectable to the main portion 201. The proximal chamber 205 may contain air and may be vented such that the pressure within the proximal chamber 205 is equal or close to the local atmosphere pressure in which the probe assembly 100 is situated. Such venting may be accomplished through a dedicated vent mechanism such as an opening in the proximal portion 202 between the proximal chamber 205 and the local atmosphere. In another configuration, such venting may be accomplished by not sealing a particular component that passes through a wall of the proximal portion 202. For example, the cable 102, which enters into the proximal chamber 205, may be configured to allow air to enter or leave the proximal chamber 205 in the area where the cable 102 enters into the proximal chamber 205.

As may be appreciated, if the enclosed volume 204 was completely surrounded by substantially rigid members and filled with fluid, temperature variations of the probe assembly 100 could result in unwanted changes in pressure within the enclosed volume 204. For example, in such a configuration, if the probe assembly 100 was exposed to elevated temperatures, the pressure of the fluid within the enclosed volume 204 may increase; possibly causing some of the fluid to leak out of the enclosed volume 204. Likewise for example, if the probe assembly 100 was exposed to reduced temperatures, the pressure of the fluid within the enclosed volume 204 may decrease, possibly causing some air to leak into the enclosed volume 204. Accordingly, it may be beneficial to prevent or reduce pressure variations within the enclosed volume 204 relative to the environmental conditions in which the probe assembly 100 is located.

To the assist in equalizing pressure between the fluid within the enclosed volume 204 and surrounding conditions, a bellows member 210 may be incorporated into the probe assembly 100. The bellows member 210 may be a generally flexible member that is collapsible and expansible in response to volumetric changes in the fluid within the enclosed volume 204, such as volumetric changes as a result of temperature changes. The bellows member 210 may be configured to define an internal volume and have a single opening. The single opening may be an open end 211 of the bellows member 210 such that the open end 211 may be disposed along the base member 203 and oriented such that the internal volume of the bellows member 210 is in communication with the proximal chamber 205. The remaining portion of the bellows member 210 may be disposed within the enclosed volume 204 and may include a closed end portion.

The initial configuration of the bellows member 210 may be selected such that the bellows member 210 is operable to compensate for (e.g., equalize pressure between a enclosed volume 204 and the proximal chamber 205) temperature variations across the operational range of temperatures for the probe assembly 100. Moreover, the bellows member 210 may be configured to compensate for temperature variations greater than the operational range of temperatures for probe assembly 100, such as temperature variations that may be seen during probe assembly 100 storage and/or transportation. The bellows member 210 may be curved or otherwise shaped to avoid other internal components within the enclosed volume 204.

At the maximum fluid temperature for which the bellows member 210 is designed to compensate, the bellows member 210 may be totally collapsed or close to being totally collapsed. In this regard, the expansion of the fluid within the enclosed volume 204 may not result in a pressure increase within the enclosed volume 204 since the bellows member 210 collapse may compensate for the expansion of the fluid. At the minimum fluid temperature for which the bellows member 210 is designed to compensate, the bellows member 210 may be expanded at or near its expansion limit. In this regard, the volumetric contraction of the fluid within the enclosed volume 204 may not result in a pressure decrease within the enclosed volume 204 since the bellows member 210 expansion may compensate for the contraction of the fluid. Furthermore, by positioning the bellows member 210 in the enclosed volume 204 and having it filled with air, less fluid is required to fill the enclosed volume 204 then would be required using a typical fluid-filled bellows external to the enclosed volume 204.

To produce the probe assembly 100 such that the enclosed volume 204 contains an amount of fluid preselected to enable the bellows member 210 to compensate for volumetric variations of the fluid over a predetermined pressure range, the following filling procedure may be used. A first step in preparation of the filled enclosed volume 204 may be to ensure that both the components to be filled and the fluid are at a known temperature. In this regard, the density of fluid at the known temperature will be known and a corresponding volume of fluid may be chosen such that the bellows member 210 may be operable to compensate for the maximum and minimum fluid temperature conditions discussed above. For example, the known temperature may be chosen to be 22° C. The next step may be to completely fill the enclosed volume 204 with fluid with the bellows member 210 in a completely collapsed condition. In such a state, at the known temperature, the exact amount of fluid within the enclosed volume 204 is known. The fluid may be delivered into the enclosed volume 204 through a sealable port 212. A measured amount of fluid may then be removed from the enclosed volume 204. The amount of fluid removed may correspond to the desired amount of expansion of the bellows member 210. The internal volume of the bellows member 210 may then be expanded such that the fluid completely fills the remaining portion of the enclosed volume 204. The bellows member 210 may be expanded by, for example, mechanically inserting an object into the bellows member 210 through the open end 211 until the fluid level within the enclosed volume 204 completely fills the enclosed volume 204. This may be determined by observing that there is no air pocket visible through the sealable port 212 and that the fluid level is coincident with the sealable port 212. In one embodiment, a seal member 213 may then be placed in the sealable port 212 such that the enclosed volume 204 is completely sealed. This method is capable of producing a sealed and filled probe assembly 100 with the correct amount of fluid therein such that the bellows member 210 may then be operable to volumetrically compensate for temperature variations over a predetermined range.

In an embodiment, the bellows 210, or at least a distal portion thereof, may be elastically-deformable. In particular, the bellows 210 may be operable to stretch or elastically expand beyond a neutral state (e.g., a state where there is no pressure differential between the inside of the bellows 210 and the outside of the bellows 210) in reaction to a pressure differential between the enclosed volume 204 and the proximal chamber 205 where the pressure within the proximal chamber 205 is greater than the pressure within the enclosed volume 204. Such stretching or elastic expansion may accommodate greater pressure differentials than would be attainable with a similarly sized bellows 210 that was substantially incapable of stretching or elastically expanding. Furthermore, such a stretchable or elastically expandable bellows 210 may result in a probe assembly 100 that is capable of withstanding a greater range of fluid volumes (e.g., the probe assembly 100 with a stretchable or elastically expandable bellows 210 may be more tolerant of a wider range of ambient temperatures, extending particularly the low temperature range where the fluid typically contracts more than the case 101). Such a stretchable or elastically expandable bellows 210 may be silicone based and may be produced using, for example, a liquid transfer molding process.

In one embodiment, a resilient, elastically-deformable bellows 210 may be provided so that in a neutral state the bellows 210 automatically assumes an initial configuration. Such initial configuration may correspond with a preformed configuration (e.g. a bulbous, dropper-shaped configuration), except as spatially restricted by other rigid componentry (e.g., bubble trap 301, main portion 201, and/or base member 203). In turn, the bellows 210 may collapse when the fluid expands at high temperature and automatically expand and stretch relative to such initial configuration in response to low temperatures.

Figure 3:
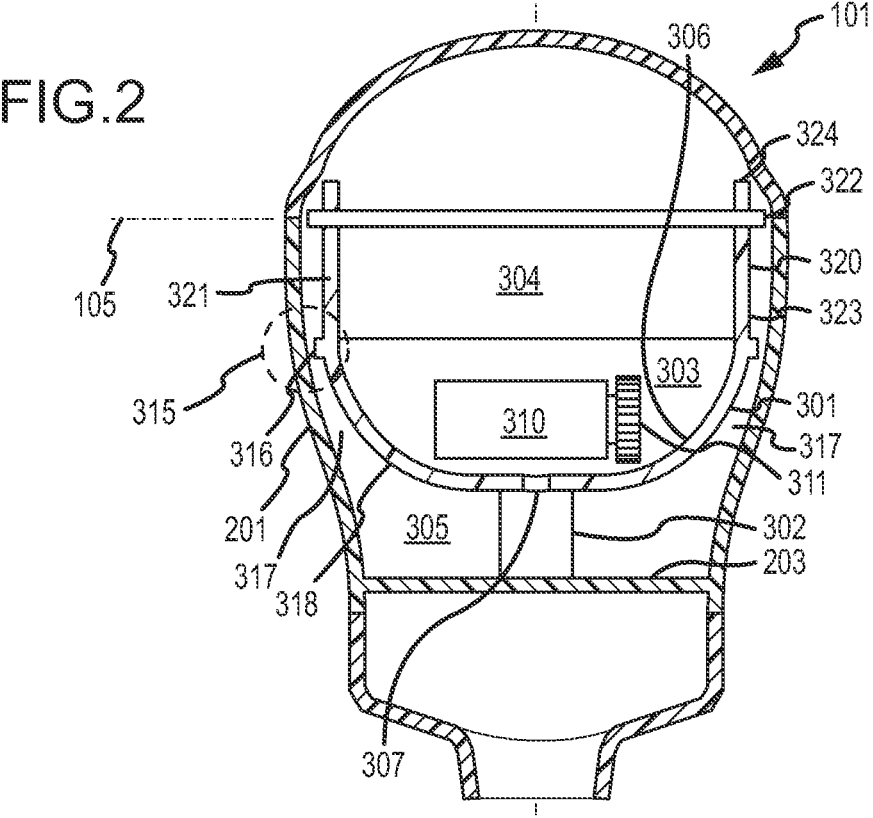
FIG. 3 is another partial cross-sectional view of selected components of the ultrasound probe assembly of FIG. 1 that includes a bubble-trap.

FIG. 3 is a partial cross-sectional view of the case 101 and a bubble-trap 301. Additional internal components of the probe assembly 100 are also illustrated in FIG. 3. The bubble-trap 301 may be interconnected to the main portion 201 of the case 101 along the base member 203. In this regard, the attachment of the bubble-trap 301 at the base member 203 may be the only portion of the bubble-trap 301 that is mechanically connected to the case 101. Thus, the bubble-trap 301 may be considered to be cantilevered from the base member 203. The bubble-trap 301 may be interconnected to the base member 203 through at least one cantilevered support 302.

The bubble-trap 301 may include a recess 303 defined by a distal-facing concave surface 306. Furthermore, a distal portion 304 of the enclosed volume 204 is defined as the portion of the enclosed volume 204 distal to the distal facing concave surface 306. Correspondingly, a proximal portion 305 of the enclosed volume 204 is defined as the portion of the enclosed volume 204 proximal to the a proximal-facing convex surface 318 of the bubble-trap 301 where the convex surface 318 is disposed on the opposite side of the bubble-trap 301 from the distal-facing concave surface 306. The bubble-trap 301 may include an aperture 307 that fluidly interconnects the distal portion 304 to the proximal portion 305. The aperture 307 may be disposed at or near the most proximal portion of the distal facing concave surface 306.

A motor 310 may be at least partially disposed with in the recess 303. The motor 310 may be operable to reciprocally pivot a transducer array 401 discussed below with reference to FIG. 4. The motor 310 may be an electrically powered motor operable to rotate an output wheel 311 in both clockwise and counterclockwise directions. The output wheel 311 may contain a plurality of teeth to engage a toothed timing belt 603 discussed below with reference to FIG. 6. The motor 310 may be mounted to the bubble-trap 301 in any appropriate manner.

In one approach, electrical signal lines (not shown) may extend from the motor 310 sealably through both the bubble trap 301 and the base member 203. Such electrical signal lines may be electrically interconnected via cable 102 to a motor controller and motor driver located at an ultrasound imaging apparatus.

Figure 8A:
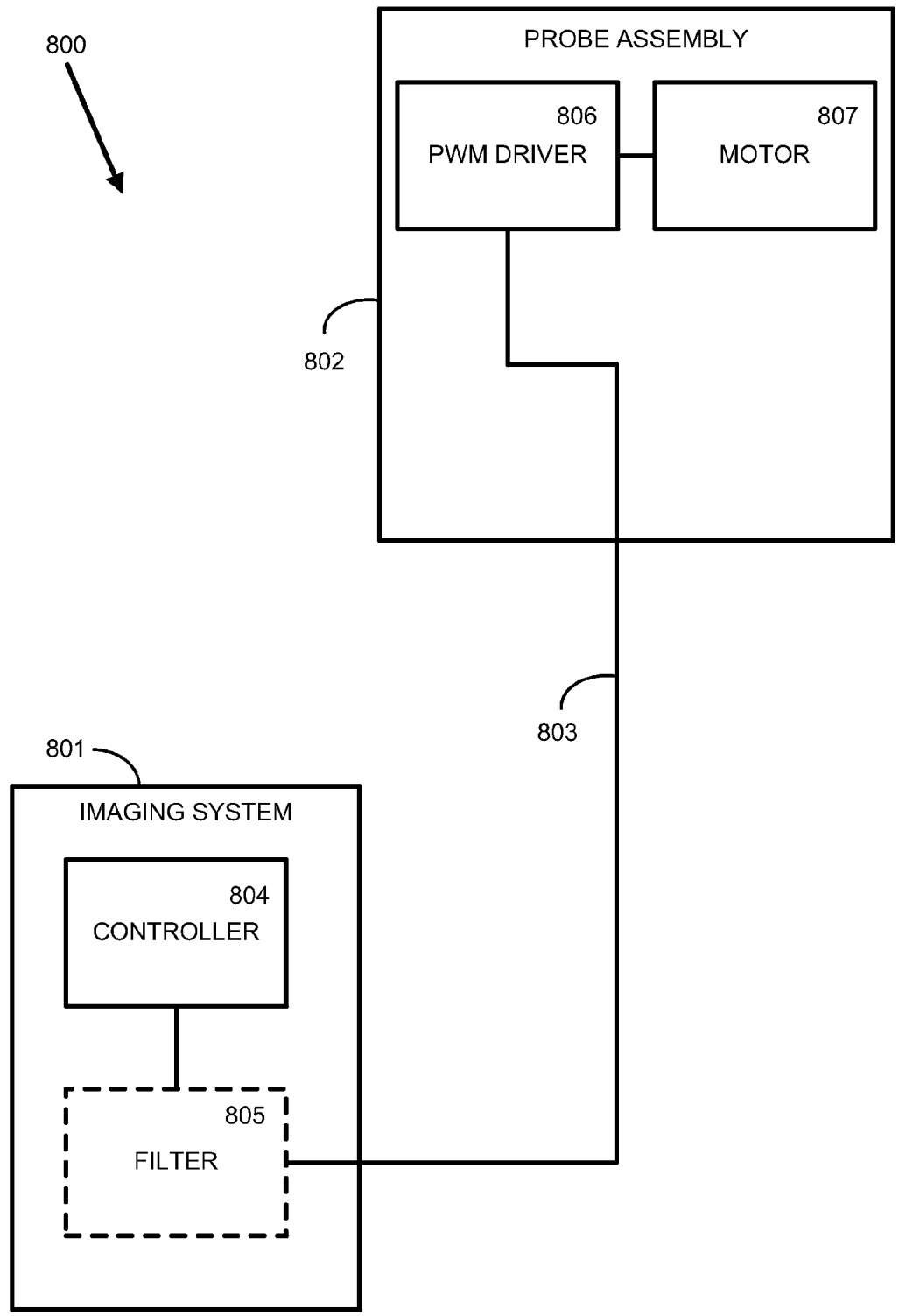
FIGS. 8A-8C are block diagrams of embodiments of an external ultrasound probe imaging system.
Figure 8B:
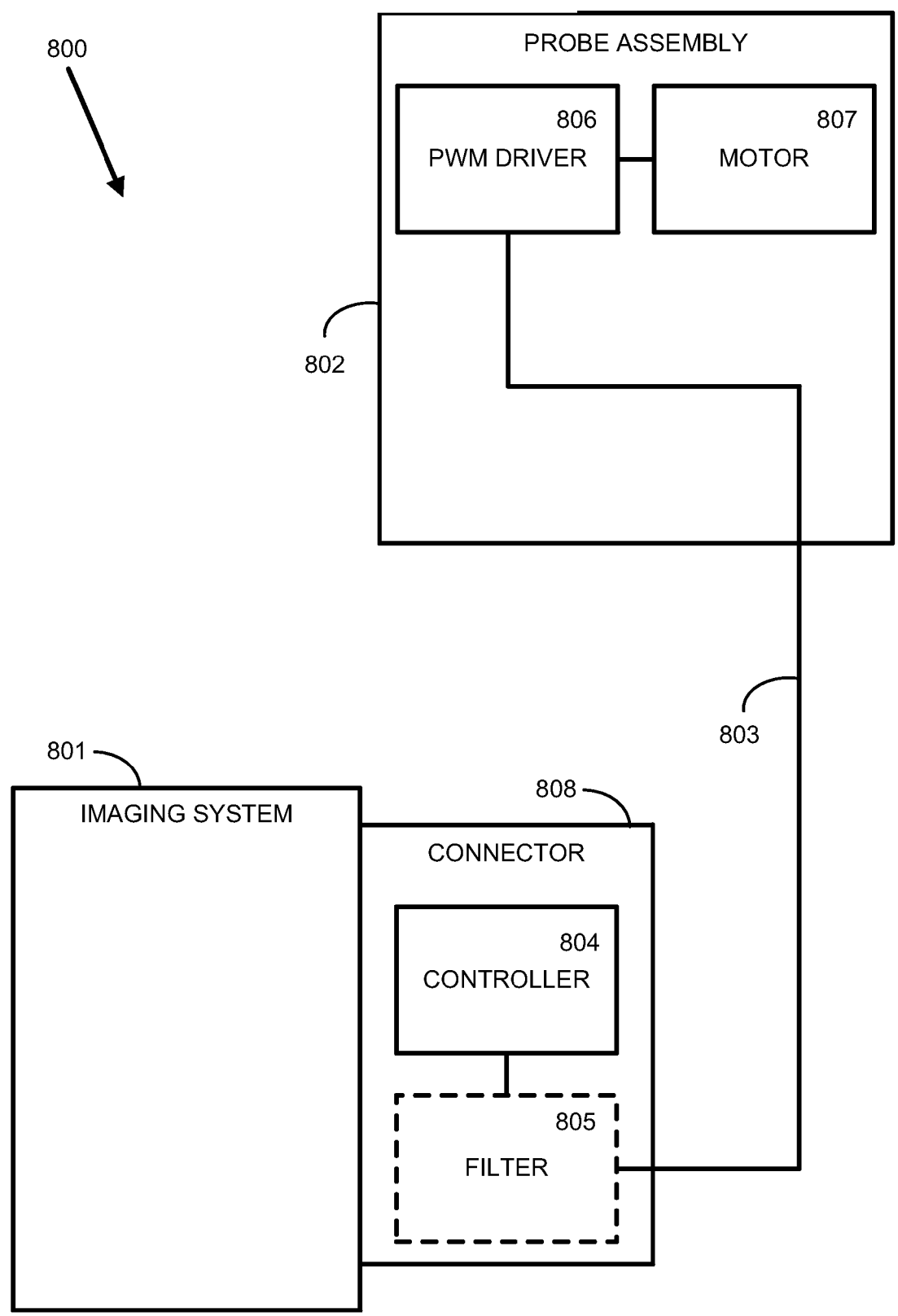
Figure 8C:
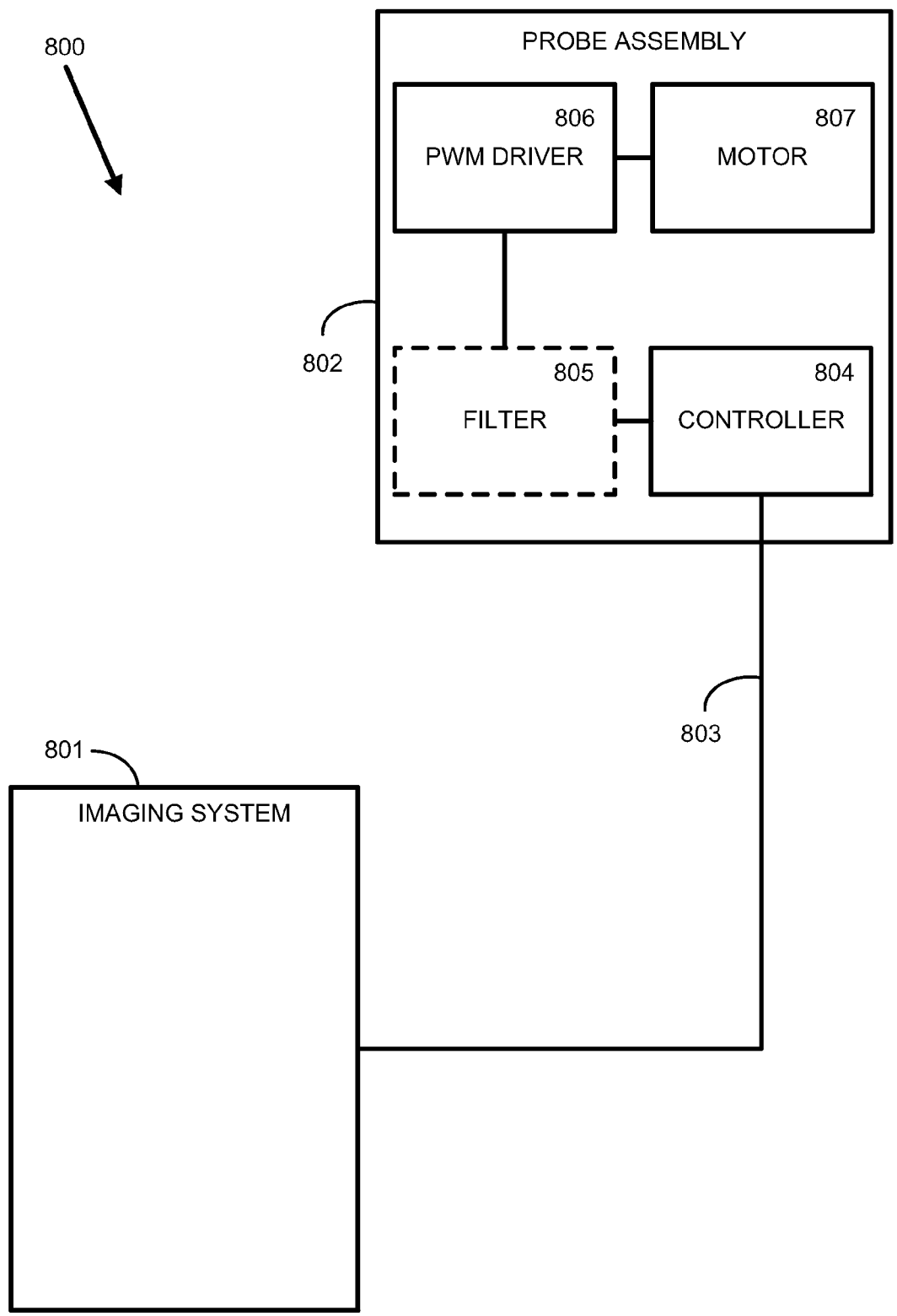

FIGS. 8A-8C are block diagrams of embodiments of an external ultrasound probe imaging system 800 that may incorporate the external ultrasound probe assemblies discussed herein. Generally, the external ultrasound probe imaging system 800 includes an imaging system 801, a probe assembly 802, and a cable 803 interconnecting the imaging system 801 to the probe assembly 802. The imaging system 801 is operable to control the external ultrasound probe imaging system 800 and drive an ultrasonic transducer array (not shown in FIGS. 8A-8C) disposed in the probe assembly 802.

To drive a motor 807 (e.g. a stepper motor or a DC motor) for reciprocal motion of the ultrasonic transducer array, the imaging system 801 may send command signals to a controller 804. The controller 804 accepts command input from the imaging system 801 regarding the required velocity, acceleration, and motion direction and translates this into control signals that will result in proper motion of the motor 807, and in turn, the output wheel 311. The controller 804 may then send the control signals in the form of low voltage digital signals to a PWM driver 806 disposed within the probe assembly 802. For example, in one embodiment the PWM driver 806 may be located within the enclosed volume 204 (e.g., within the recess 303) or proximal chamber 205 (FIG. 2). Placing the PWM driver 806 in the probe assembly 802, as compared to placing a PWM driver external to the probe assembly 100, reduces the current and voltage of the signal to the motor 807 through the system cable 803. The PWM driver 806 may be shielded from the transducer array via the positioning of a shield member therebetween (e.g. a brass shield). The inclusion of the PWM driver 806 within the probe assembly 802 reduces signal isolation requirements within the cable 803.

An optional filter 805 may be disposed between the controller 804 and the PWM driver 806 to reduce interference (e.g., by reducing high frequency content) between the low voltage output signals of the controller 804 and the ultrasound signals. The PWM driver 806 may receive the low voltage control signals (e.g., step and direction signals) from the controller 804 to produce high current PWM signals to drive the motor 807 (e.g., excite the motor 807 windings).

FIG. 8A illustrates an embodiment where the controller 804 and the optional filter 805 are disposed in the imaging system 801. In such a configuration, the cable 803 communicates the low voltage digital signals from the imaging system to the PWM driver 806.

FIG. 8B illustrates an embodiment where the controller 804 and the optional filter 805 are disposed in a connector 808 that is part of the cable 803 and is connectable to the imaging system 801. Such a configuration may advantageously be connectable and compatible with a variety of imaging systems. As with the configuration of FIG. 8A, the cable 803 communicates the low voltage digital signals from the imaging system 801 to the PWM driver 806.

FIG. 8C illustrates an embodiment where the controller 804 and the optional filter 805 are disposed in the probe assembly 802. The controller 804 and optional filter 805 may be located, for example, within the enclosed volume 204 or proximal chamber 205 (FIG. 2). In such a configuration, the cable 803 may carry the command signals from the imaging system 801 to the controller 804. As with the configuration of FIG. 8B, such a configuration may advantageously be connectable and compatible with a variety of imaging systems. In particular, where the controller 804 is placed in the probe assembly 802 with the PWM driver 806, the filter 805 may not be required since the signals may be isolated from the ultrasound signals by local shielding.

The bubble-trap 301 may be disposed such that there is a region of minimum clearance 315 between the bubble-trap 301 and the main portion 201. The bubble-trap 301 may contain a peripheral rim or circumferential rib 316 or similar feature such that the region of minimum clearance 315 is disposed between the rib 316 or similar feature and the main portion 201. Alternatively, the rib 316 may be part of the main portion 201. The minimum clearance distance between the bubble-trap 301 and the main portion 201 may be selected such that an air bubble present in the fluid would be incapable of passing through the region of minimum clearance 315. As will be appreciated, the minimum clearance required such that an air bubble in the fluid may not pass through the region of minimum clearance 315 may be dependent on several factors including, but not limited to, the viscosity of the fluid, the surface textures of the bubble-trap 301, bubble size, and main portion 201 in the region of minimum clearance 315, and the materials from which the bubble-trap 301 and main portion 201 are constructed. In any case, the capillary forces causing the fluid to adhere to the surfaces must exceed the buoyancy force of the air bubble.

In another embodiment, a gasket member 513 (shown in FIG. 5) may be disposed along the rib 316 of the bubble trap 301 to assist in inhibiting bubbles from passing between the rib 316 and the main portion 201 (e.g., from the proximal portion of the enclosed volume 305 to the distal portion of the enclosed volume 304). The gasket member 513 may be constructed from a lubricious material to allow for relative movement between the bubble trap 301 and the main portion 201. Allowing such relative movement may be beneficial in that impact (e.g., from the probe assembly 100 being dropped onto a hard surface) resistance of the probe assembly 100 may be enhanced. The gasket member 513 may comprise a lubricious, conformable and compressible material such as ePTFE.

During assembly, the gasket member 513 may be placed around the bubble trap 301 along the rib 316 and the bubble trap 301 may be inserted into the main portion 201 such that the gasket member 513 is disposed between the rib 316 and the main portion 201. A portion of the gasket member 513 where the rib 316 is closest to the main portion 201 may be deformed or crushed during the assembly process. The remainder of the gasket member 513 may remain undeformed or uncrushed. In this regard, the gasket member 513 may conform to the region between the rib 316 and the main portion 201 and may inhibit bubbles from passing between the rib 316 and the main portion 201. Furthermore, resilient members 703 (shown in FIG. 7), for example, O-rings, may be interposed between the bubble trap 301 and the base member 203 and/or between the undersides of fasteners 704 (attached to the bubble trap 301) and the base member 203. During attachment of the bubble trap 301 to the base member 203, the resilient members 703 may be partially compressed.

As noted above, the lubricious nature of the gasket member 513 may allow for relative movement between the bubble trap and the main portion 201. Moreover, the resilient nature of the resilient members 703 may also allow relative movement between the bubble trap 301 and the base member 203 (which is rigidly interconnected to the main portion 201). Together, the gasket member 513 and resilient members 703 may operate to increase impact resistance of the probe assembly 100. For example, upon impact (e.g., from a drop onto a hard surface), the resilient members 703 may compress and/or expand to absorb some of the energy from the impact while the gasket member 513 may allow for the relative movement of the bubble trap 301 and the main portion 201 such that the bubble trap 301 may slide relative to the main portion 201. Moreover, the gasket member 513 may also absorb some of the energy from the impact.

To control the motion of the bubble trap 301 relative to the main portion 201, the rib 316 of the bubble trap 301 may include a pair of notches 325 (shown in FIG. 4) configured to fit around a pair of corresponding vertical ribs 702 (shown in FIG. 7) disposed on the inner surface of the main portion 201. Together the pair of notches 325, the vertical ribs 702, the resilient members 703, and the gasket member 513 combine to restrict the motion of the bubble trap 301 relative to the main portion 201 to motion generally along the central axis 107 (FIG. 1). The gasket member 513 may be placed onto the rib 316 such that it forms a single layer of material about the rib 316 (FIG. 5). Furthermore, the gasket member 513 may include a pair of seams 514 where the gasket member 513 is not continuous. The seams 514 may be located where the gasket member 513 passes over the notches 325. Accordingly, when the bubble trap 301 is inserted into the main portion 201, the portions of the gasket member 513 proximate to the notches 325 may be moved such that they are disposed within the notches 325 between the notches 325 and the vertical ribs 702. In an alternate embodiment, the gasket member 513 may initially be placed into the main portion 201, and then the bubble trap 301 may be inserted into the main portion 201.

During the life cycle of the probe assembly 100, bubbles may be formed in or enter into the enclosed volume 204. The bubble-trap 301 may be operable to trap these bubbles in the proximal portion 305 of the enclosed volume 204. For example, during normal operation of the probe assembly 100 the probe assembly may be disposed in a variety of attitudes including attitudes where the distal end 108 of the probe assembly 100 is facing downward. When the probe assembly 100 is in a downward facing attitude, a bubble within the distal portion 304 may tend to naturally flow upward. Upon coming into contact with the concave face 306, the bubble may continue to rise until it reaches the aperture 307. The bubble may then pass through the aperture 307, moving from the distal portion 304 to the proximal portion 305. Once the bubble is in the proximal portion 305 and the probe assembly 100 is placed in an attitude where the distal portion is facing upward, the convex surface 318 will tend to direct any rising bubbles in the proximal portion 305 along the convex surface 318 away from the aperture 307. Following the slope of the convex surface 318, the bubbles will tend to migrate to a trap region 317. As previously noted, a bubble in the trap region 317 may be incapable of passing between the bubble-trap 301 and the main portion 201 in the region of minimum clearance 315, and therefore may be trapped in the trap region 317.

The bubble-trap 301 may also include a first support 320. The first support 320 may support an axle 322. The axle 322 may be fixedly interconnected to the support 320 as shown in FIG. 3. Alternatively, the first support 320 may include a bearing member (not present in the embodiment of FIG. 3) operable to allow the axle 322 to be rotatably interconnected to the support member 320. The first support 320 may have a proximal portion 323 interconnected to the portion of the bubble-trap 301 that defines the recess 303. The first support 320 may have a distal portion 324 distal to the portion of the bubble-trap 301 that defines the recess 303. As will be appreciated, as shown in FIG. 3 the first support 320 is fixedly positioned relative to the case 101. In this regard, the bubble-trap 301 may be a rigid member that includes the first support 320 and the cantilevered support 302, and the fixed attachment of the cantilevered support 302 to the base member 203 of the case 101 may be the only attachment point of the bubble-trap 301 to the case 101. Thus the first support 320 and the axle 322 may be fixedly positioned relative to the case 101 within the enclosed volume 204. The first support 320 may be disposed such that it is generally parallel to the central axis 107.

As shown in FIG. 3, the bubble-trap 301 may include a second support 321 that is configured similarly to the first support 320. In this regard, the first support 320 and the second support 321 may each fixedly support opposing end of the axle 322. The support members 320, 321 may be spaced apart from each other on opposing sides of the central axis 107. The support members 320, 321 may be disposed parallel to each other and parallel to the central axis 107. The axle 322 may be disposed normal to the central axis 107 and parallel to the longitudinal axis 105.

A filter may be disposed across the aperture 307. The filter may be configured such that gasses (e.g., air) may pass through the filter while liquid (e.g., oil, saline) may not be able to pass through the filter. Such a configuration may allow air bubbles to pass from the distal portion of the enclosed volume 304, through the filter disposed across the aperture 307, and into the proximal portion of the enclosed volume 305, while preventing fluid from passing through the filter disposed across the aperture 307. The filter may include ePTFE.

Figure 4:
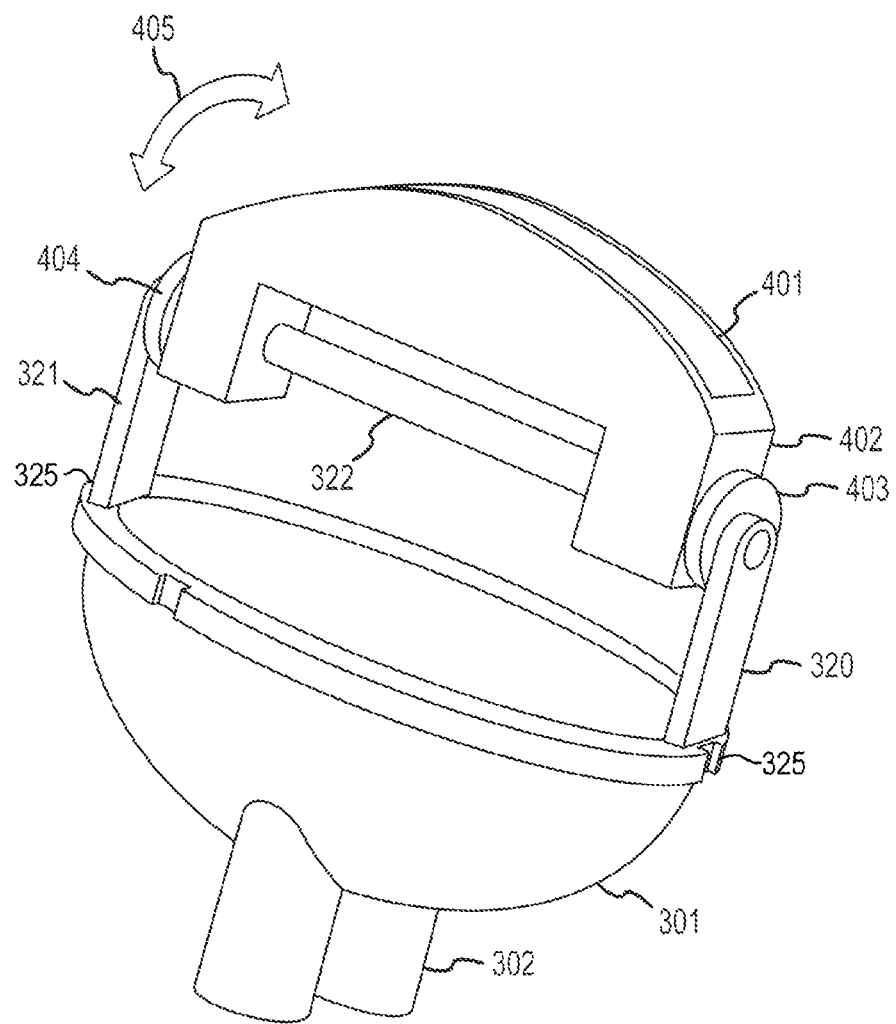
FIG. 4 is an isometric view of the bubble-trap and a transducer array of the ultrasound probe assembly of FIG. 1.
Figure 5:
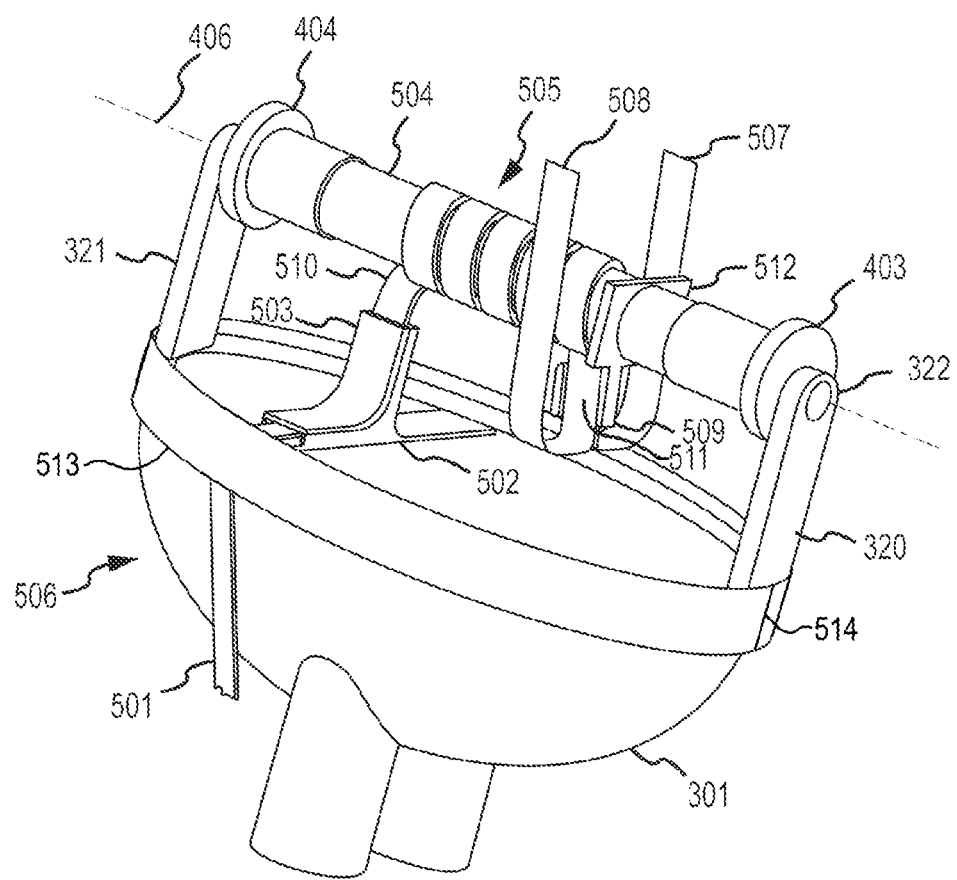
FIG. 5 is an isometric view of the bubble-trap and an electrical interconnection member of the ultrasound probe assembly of FIG. 1.

FIG. 4 is an isometric view of the bubble-trap 301 and axle 322 of FIG. 3 along with a transducer array 401 and associated support structure. For clarity of explanation, the case 101 is not shown in FIG. 4. The transducer array 401 may be a mechanically active layer operable to convert electrical energy to mechanical (e.g., acoustic) energy and/or convert mechanical energy into electrical energy. For example, the transducer array 401 may comprise a plurality of piezoelectric elements. For example, the transducer array 401 may be operable to convert electrical signals from the ultrasound imaging apparatus into ultrasonic acoustic energy. Furthermore, the transducer array 401 may be operable to convert received ultrasonic acoustic energy into electrical signals.

The transducer array 401 may comprise an array of individual transducer elements that may each be electrically connected to the ultrasound imaging apparatus via a signal connection and a ground connection. The transducer array 401 may be a one-dimensional array that includes a single row of individual transducer elements. The transducer array 401 may be a two-dimensional array that includes individual transducer elements arranged, for example, in multiple columns and multiple rows. Ground connections of the entire transducer array 401 may be aggregated and may be electrically connected to the ultrasound imaging apparatus through a single ground connection.

To generate an ultrasound image, the ultrasound imaging apparatus may send electrical signals to the transducer array 401 which in turn may convert the electrical energy to ultrasonic acoustic energy 104 which may be emitted toward the image volume 109. Structure within the image volume 109 may reflect a portion of the acoustic energy back toward the transducer array 401. The reflected acoustic energy may be converted to electrical signals by the transducer array 401. The electrical signals may be sent to the ultrasound imaging apparatus where they may be processed and an image of the image volume 109 may be generated.

The probe assembly 100 may be operable to scan the image volume 109. This may be accomplished by mounting the transducer array 401 on a transducer array frame 402 and mechanically sweeping (e.g., reciprocally pivoting) the transducer array frame 402 about a pivot axis 406. The pivot axis 406 may correspond to the longitudinal axis of the axle 322. The pivot axis 406 may be parallel to or coincident with the longitudinal axis 105 described with reference to FIG. 1. Thus, through a combination of electronic sweeping along the longitudinal axis 105 and mechanical sweeping of the transducer array 401 about the pivot axis 406, beams of acoustic energy may be swept through the image volume 109. Energy reflected back to the transducer array may be converted into a three-dimensional image of the imaging volume 109.

As noted above, the enclosed volume 204 may be fluid filled. The fluid may act to acoustically couple the transducer array 401 to the sonolucent distal portion 104 of the case 101 of FIG. 1.

As noted, the transducer array 401 may be supported by the transducer array frame 402. In turn, the transducer array frame 402 may be rotatably interconnected to the axle 322 such that the transducer array 401 may be operable to be reciprocally pivoted about the axle 322 and the pivot axis 406 as illustrated by arrow 405. The rotatable interconnection may be achieved through the use of one or more bearing members such as a first bearing member 403 and a second bearing member 404. The bearing members 403, 404 may be fixedly interconnected to the transducer array frame 402 in any appropriate manner (e.g., press fit, clamped). The bearing members 403, 404 may allow the transducer array frame 402 to freely pivot about the axle 322. Any appropriate number of bearing members may be used to rotatably interconnect the transducer array frame 402 to the bubble-trap 301.

As will be appreciated, the transducer array 401, by virtue of its interconnection to the axle 322 and bubble-trap 301 is supportably cantilevered from the base member 203.

FIG. 5 is an isometric view of the bubble-trap 301 and an electrical interconnection member 501. For clarity of explanation, other components are not shown in FIG. 5. The electrical interconnection member 501 may electrically interconnect the transducer array 401 (not shown in FIG. 5) with the ultrasound imaging apparatus. The electrical interconnection member 501 may be a multi-conductor cable comprising of a plurality of conductors arranged side-by-side with electrically nonconductive material between the conductors. The electrical interconnection member 501 may be ribbon shaped. For example, the electrical interconnection member 501 may comprise one or more GORE™ Microminiature Flat Cables.

The electrical interconnection member 501 may be anchored such that a portion of it is fixed relative to the bubble-trap 301. To accomplish this, the electrical interconnection member 501 may be secured to a cable anchor base 502. The cable anchor base 502 may be fixedly interconnected to the bubble-trap 301. Any appropriate method of anchoring the electrical interconnection member 501 to the cable anchor base 502 may be used. In one exemplary construction, the electrical interconnection member 501 is secured to the cable anchor base 502 by sandwiching the electrical interconnection member 501 between a cable anchor member 503 and the cable anchor base 502. For example, the electrical interconnection member 501 may be placed into a channel of the cable anchor base 502 and the cable anchor member 503 may be snapped or otherwise attached to the cable anchor base 502 thereby securing the electrical interconnection member 501. Such an arrangement delineates a first portion 505 of the electrical interconnection member 501 that moves relative to the bubble-trap 301 (and therefore also moves relative to the case 101) from a second portion 506 of the electrical interconnection member 501 that is fixed relative to the bubble-trap 301.

The cable anchor base 502 may secure the electrical interconnection member 501 in such a manner that a portion of the electrical interconnection member 501 where it emerges from the cable anchor base 502 is generally directed toward the axle 322 around which the transducer array 401 pivots. Furthermore, where the electrical interconnection member 501 is ribbon shaped, the width of the ribbon may be disposed generally parallel to the pivot axis 406. In an alternate embodiment, the width of the ribbon may be disposed generally perpendicular to the pivot axis 406.

Since, during scanning, the transducer array 401 may be pivoted about the pivot axis 406 relative to the bubble-trap 301 and the case 101, the electrical interconnection member 501 must be operable to maintain an electrical connection to the transducer array 401 while the transducer array 401 is pivoting relative to the cable anchor base 502 to which the electrical interconnection member 501 is fixed. This may be achieved by coiling the electrical interconnection member 501 about the pivot axis 406. A first end of the coil 510 may be anchored by the cable anchor base 502. A second end of the coil 511 may be anchored to a member, such as an outer shaft 504 (described below) that pivots along with the transducer array 401 about the pivot axis 406. Where the electrical interconnection member 501 is ribbon shaped, the electrical interconnection member 501 may be disposed such that a top or bottom side of the ribbon faces and wraps about the pivot axis 406.

The outer shaft 504 may be configured such that it is operable to rotate about the pivot axis 406. The outer shaft 504 may contain a feature, such as a protruding portion 512, that may interact with the transducer array frame 402 such that the outer shaft 504 is fixed relative to the transducer array frame 402. The outer shaft 504 may also contain an electrical interconnection member outer shaft anchor 509 that is operable to anchor the electrical interconnection member 501 to the outer shaft 504. The electrical interconnection member outer shaft anchor 509 may be positioned such that it is operable to anchor the second end of the coil 511 to the outer shaft 504. Once the electrical interconnection member 501 is fixed relative to the transducer array 401 (e.g., at the electrical interconnection member outer shaft anchor 509) it may be directed toward electrical interconnection with the transducer array 401. As illustrated in FIG. 5, a first distal end 507 of the electrical interconnection member 501 may be disposed such that it is operable to be electrically interconnected to the transducer array 401. Although the actual interconnection of the electrical interconnection member 501 to the transducer array 401 is not illustrated in FIG. 5, any appropriate known method of attaching a plurality of conductors to a transducer array may be used for the interconnection.

As illustrated in FIG. 5, the electrical interconnection member 501 may be made up of a plurality of ribbons, each of which includes multiple conductors separated by insulating material. The plurality of ribbons may be wound around the outer shaft 504 in a face-to-face relationship. Once anchored to the outer shaft 504, the individual ribbons may be separated for interconnection to the transducer array 401 at a plurality of different locations. For example, as shown in FIG. 5, the electrical interconnection member 501 may comprise two unique ribbon portions (e.g., a first electrical interconnection member and a second electrical interconnection member) that may be directed from the electrical interconnection member outer shaft anchor 509 to opposing sides of the outer shaft 504. The individual ribbons may then be directed toward the transducer array 401 such that they are disposed in parallel planes on opposing sides of the pivot axis 406. Accordingly, the individual ribbons may interconnect to the transducer array 401 at a first ribbon distal end 507 and at a second ribbon distal end 508 along opposing sides of the transducer array frame 402.

FIG. 5 illustrates a configuration where the electrical interconnection member 501 is helically disposed within the enclosed volume 204. The electrical interconnection member is helically disposed about the outer shaft 504 where the outer shaft 504 pivots along with the transducer array 401. In other embodiments, the electrical interconnection member 501 may coil about a stationary shaft, the first end of the coil 510 may be fixedly connected to a portion of the stationary shaft, and the second end of the coil 511 may be interconnected to a component that pivots along with the transducer array 401.

As noted, the electrical interconnection member 501 includes a first portion 505 that is coiled about the pivot axis 406 (e.g., the longitudinal axis of the axle 322) of the transducer array 401. The electrical interconnection member 501 may be coiled about the pivot axis 406 a plurality of times. The electrical interconnection member 501 may be coiled about the pivot axis 406 such that the electrical interconnection member 501 forms a helix about the pivot axis 406. By coiling the electrical interconnection member 501 about the pivot axis 406 a plurality of times, undesirable counteracting torque on the pivoting of the transducer array 401 may be significantly avoided. Pivoting of the transducer array 401 about the pivot axis 406 in such a configuration may result in a slight tightening, or slight loosening, of the turns of the coiled first portion 505 of the electrical interconnection member 501. Such a slight tightening and loosening may result in each coil (e.g., each individual rotation of the helix about the pivot axis 406) producing only a small lateral displacement and corresponding displacement of fluid. Furthermore, the displacement may not be uniform for each coil of the helix. Furthermore, by distributing the movement of the first portion 505 of the electrical interconnection member 501 over a plurality of coils, the mechanical stresses of movement are distributed over the entire helically disposed first portion 505. Distributing mechanical stresses may result in longer mechanical life for the electrical interconnection member 501. The helically disposed portion of the electrical interconnection member 501 may be helically disposed in a non-overlapping manner (e.g., no portion of the electrical interconnection member 501 may overlie itself in the region of the helix).

Figure 6:
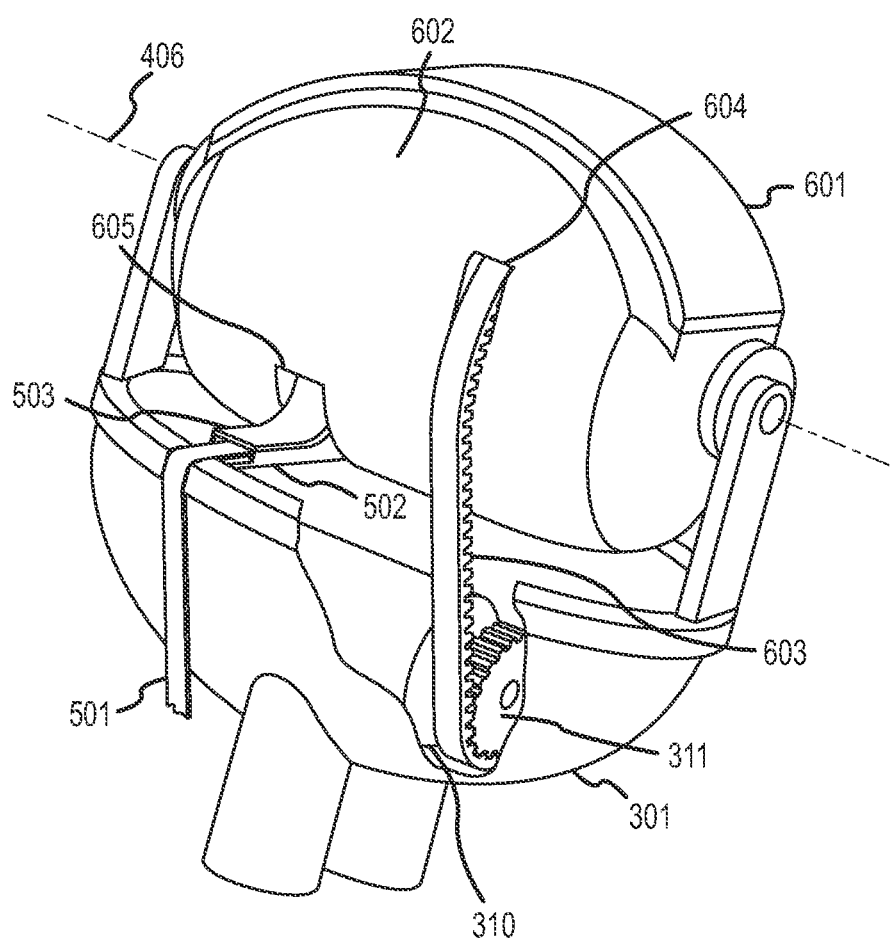
FIG. 6 is an isometric view of the bubble-trap and a shell member of the ultrasound probe assembly of FIG. 1.

FIG. 6 is an isometric view of the bubble-trap 301 along with an acoustic lens 601 and a shell member 602. For clarity of explanation, some components are not shown in FIG. 6.

The configuration of FIG. 6 includes the transducer array 401 and the transducer array frame 402 shown in FIG. 4. However, these components are not visible in FIG. 6 since they are encased within the acoustic lens 601 and the shell member 602.

The acoustic lens 601 may be constructed of a single lens element bonded to the transducer array 401. Alternatively, the acoustic lens 601 may be comprised of a plurality of lens elements. The acoustic lens may be operable to focus acoustic waves generated at, and moving perpendicular to, an acoustic face of the transducer array 401. The acoustic characteristics of the acoustic lens 601 may be selected based at least in part on the acoustic characteristics of to fluid within the enclosed volume 204, the acoustic properties of the sonolucent distal portion 104, the acoustic properties of the volume to be imaged (e.g., a patient), or any combination thereof. The outer surface of the acoustic lens 601 may be an arcuate surface that corresponds to the inner surface of the sonolucent distal portion 104.

The shell member 602 may at least partially enclose the transducer array frame 402 and the coiled first portion 505 of the electrical interconnection member 501. The outer surface of the shell member 602 may be an arcuate surface that at least partially conformally adjoins the arcuate surface of the acoustic lens 601. In this regard, the outer surface of the shell member 602 may be streamlined to reduce resistance as the shell member 602, the acoustic lens 601, the transducer array 401 and the transducer array frame 402 are pivoted back-and-forth through the fluid contained in the enclosed volume 204. Together, the shell member 602 and the acoustic lens 601 may generally define an ellipsoid.

The shell member 602 may comprise a single unitary element or it may be comprised of a plurality of individual sections that are assembled together. The shell member 602 may include a timing belt anchor point 604 to which a timing belt 603 is anchored. The anchoring of the timing belt 603 to the timing belt anchor point 604 may be configured in any appropriate manner. For example, in the case where the shell member 602 is made of a plurality of individual sections, the timing belt anchor point 604 may be created by clamping two individual sections of the shell member 602 about a portion of the timing belt 603. In another example, the timing belt 603 may be glued or otherwise bonded to the shell member 602.

The timing belt 603 may operatively connect the output wheel 311 of the motor 310 to the shell member 602. Accordingly, as the motor 310 causes the output wheel 311 to rotate, a corresponding rotation will be produced in the shell member 602 and the transducer array 401. As illustrated in FIG. 6, the timing belt 603 and output wheel 311 may have corresponding toothed arrangements. In this regard, when motor 310 position is known, the corresponding position of the transducer array 401 will be known. Motor 310 position may be tracked in any appropriate manner, such as through the use of an encoder.

The shell member 602 may include a slot 605 for clearance around the electrical interconnection member 501 in the area where the electrical interconnection member 501 transitions from the outside of the shell member 602 to the inside of the shell member 602. The length of the slot 605 in a direction perpendicular to the pivot axis 406 may be selected to correspond to the maximum amount of rotation of the shell member 602. The width of the slot 605 may correspond to the width of the cable anchor base 502 and cable anchor member 503 assembly.

Figure 7:
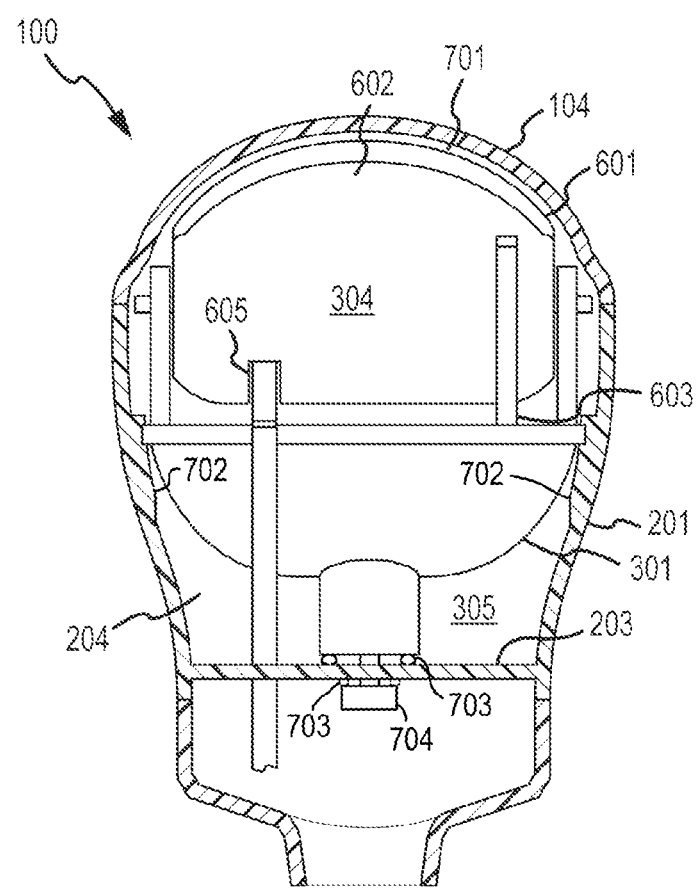
FIG. 7 is another partial cross-sectional view of selected components of the ultrasound probe assembly of FIG. 1 that includes the bubble-trap and the shell member.

FIG. 7 is a view of a portion of the probe assembly 100 that includes, inter alia, the case 101, the bubble-trap 301, the acoustic lens 601 and the shell member 602. The case 101 is shown in cross-section.

As noted above, the bubble-trap 301 may be configured to allow bubbles to pass from the distal portion 304 of the enclosed volume 204 to the proximal portion 305 of the enclosed volume 204 through the aperture 307 (not shown in FIG. 7), while inhibiting bubbles from moving from the proximal portion 305 to the distal portion 304. This configuration is beneficial since bubbles present between the acoustic lens 601 and the sonolucent distal portion 104 of the case 101 may produce unwanted image artifacts when the probe assembly 100 is used to generate an image of the image volume 109. This is due to the differing acoustical properties of an air bubble versus the acoustical properties of the fluid within the enclosed volume 204. By keeping bubbles that may form during the lifetime of the probe assembly 100 away from the acoustic lens 601, the operational life of the probe assembly 100 may be increased. In this regard bubbles that may form within the enclosed volume 204 or enter into the enclosed volume 204 may not necessarily lead to a degradation of the images created using the probe assembly 100. Furthermore, since the probe assembly 100 with the bubble-trap 301 may be tolerant to a certain level of bubbles within the enclosed volume 204, servicing and subsequent refilling and sealing of the probe assembly 100 may be easier than would be the case if the probe assembly 100 was not bubble tolerant. Accordingly, the field service of the probe assembly 100 may be simplified due to the ability of the probe assembly 100 to tolerate a certain level of bubbles within the enclosed volume 204.

As noted above, the bubble-trap 301 and the transducer array 401 and associated pivoting parts are all supportably cantilevered from the base member 203. In this regard, the internal components of the probe assembly 100 may be completely free from contact with the case 101 (including the sonolucent distal portion 104 and the main portion 201) except for interconnection to the base member 203. Consequently, as the enclosed volume 204 is fluid filled, there may therefore be a layer of fluid between the case 101 and the internal components of the probe assembly 100. This layer of fluid may result in the probe assembly 100 being more robust and able to survive mechanical shock to a greater degree when compared to a probe assembly where the case is used to structurally support internal components at a plurality of locations (e.g., where a rotational axis is supported on both ends by the outer shell of the probe assembly). In this regard, when the mechanical shock (e.g., from a drop) is imparted on the probe assembly 100, the case 101 may absorb a certain amount of the shock and the fluid between the case 101 and the internal components may also absorb a certain amount of the shock. Furthermore, the cantilevered structure supporting the internal components may absorb some of the shock.

The sonolucent distal portion 104 of the case 101 may be shaped to correspond with the curvature of the acoustic lens 601 such that a gap 701 between the sonolucent distal portion 104 and acoustic lens 601 is consistent along the longitudinal axis 105 through out the range of pivotal motion of the acoustic lens 601. Such a configuration may avoid potential image distortion that could be caused if there were a varying amount of fluid between the acoustic lens 601 and the sonolucent distal portion 104.

Various seal members may be employed in the probe assembly 100 to seal the fluid in the enclosed volume 204 and to prevent the entry of air into the enclosed volume 204. For example, an o-ring type of seal may be employed between the sonolucent distal portion 104 and the main portion 201 of the case 101. Furthermore, objects passing through the base member 203, such as mounting bolts to mount the bubble-trap 301 to the base member 203, the bellows member 210, the seal member 213 and the electrical interconnection member 501 may all employee appropriate sealing features such as, but not limited to, o-rings, gaskets, welds and/or curable sealants.

Additional modifications and extensions to the embodiments described above will be apparent to those skilled in the art. Such modifications and extensions are intended to be within the scope of the present invention as defined by the claims that follow.

What is claimed is:

1. An external ultrasound probe comprising:
    a case having an enclosed volume;
    a fluid disposed within said enclosed volume;
    a bubble-trap member fixedly positioned relative to said case within said enclosed volume and having a distal-facing, concave surface, wherein a distal portion of said enclosed volume is defined distal to said bubble-trap member and a proximal portion of said enclosed volume is defined proximal to said bubble-trap member, and wherein an aperture is provided through said bubble-trap member to fluidly interconnect from said distal portion of said enclosed volume to said proximal portion of said enclosed volume; and,
    an ultrasound transducer array supportably interconnected to said bubble-trap member and immersed in said fluid, wherein said ultrasound transducer array and said bubble-trap member are each supportably cantilevered from an end of said case proximal to said bubble-trap member and said bubble trap member and said ultrasound transducer array are otherwise free from fixed engagement with said case.

2. An ultrasound probe as recited in claim 1, further comprising:
    a first support member fixedly interconnected to said bubble-trap member within said enclosed volume; and,
    an axle fixedly supported by said support member, wherein said axle defines a pivot axis within said enclosed volume, wherein said ultrasound transducer array is pivotably supported by said axle for reciprocal pivotal movement about said pivot axis.

3. An ultrasound probe as recited in claim 2, further comprising:
    a second support member fixedly interconnected to said bubble-trap member within said enclosed volume, wherein said axle is fixedly supported by and between said first support member and said second support member.

4. An ultrasound probe as recited in claim 3, wherein said probe is of an elongate configuration having a center axis, and wherein said pivot axis is located in a plane that is substantially normal to said center axis of said probe in a distal portion of said probe.

5. An ultrasound probe as recited in claim 4, wherein said first support member and said second support member are each disposed parallel to said center axis of said ultrasound probe.

6. An ultrasound probe as recited in claim 1, further comprising a filter disposed across said aperture.

7. An ultrasound probe as recited in claim 6, wherein said filter is configured such that air may pass through said aperture, and wherein said filter is configured such that said fluid is unable to pass through said aperture.

8. An ultrasound probe as recited in claim 1, said distal-facing concave surface of said bubble trap defining a recess, and said ultrasound probe further comprising:
   a motor at least partially disposed within said recess defined by said bubble-trap member within said enclosed volume, wherein said motor is operatively interconnected to said ultrasound transducer array to affect said reciprocal pivotal movement thereof.

9. An ultrasound probe as recited in claim 8, wherein said motor is fixedly connected to said bubble-trap, wherein said bubble-trap and said motor are supportably cantilevered from a proximal end of said case.

10. An ultrasound probe as recited in claim 9, further comprising:
   a drive wheel operatively interconnected to said motor such that said motor is operable to reciprocally rotate said drive wheel; and
   a timing belt operatively interconnected to said drive wheel, wherein said timing belt is operatively interconnected to said ultrasound transducer array such that said ultrasound transducer array reciprocally pivots in response to said drive wheel reciprocally rotating.

11. An ultrasound probe as recited in claim 8, wherein said motor is disposed fully within said recess.

12. An ultrasound probe as recited in claim 1, wherein a peripheral rim of said bubble-trap is spaced a distance from said case such that a bubble within said fluid is incapable of passing between said peripheral rim of said bubble-trap and said case.

13. An ultrasound probe as recited in claim 1, wherein said bubble-trap comprises a peripheral rim, said ultrasound probe further comprising:
   a gasket member disposed between said peripheral rim of said bubble trap and said case, wherein said gasket member restricts passage of bubbles within said fluid between said peripheral rim and said case.

14. An ultrasound probe as recited in claim 13, wherein said gasket member is fixedly interconnected to one of said peripheral rim of said bubble trap and said case, and is slidable relative to the other one of said peripheral rim and said case upon relative movement therebetween.

15. An ultrasound probe as recited in claim 14, further comprising:
   a resilient member interposed between a cantilevered end of said bubble trap and said case, wherein said resilient member is compressible to permit a predetermined amount of relative movement between said bubble trap and said case.

16. An ultrasound probe as recited in claim 14, wherein said gasket member comprises expanded polytetrafluoroethylene (ePTFE).

17. An ultrasound probe as recited in claim 1, further comprising:
   a bellows member having a flexible, closed-end portion located in said fluid within said case and an open-end isolated from said fluid, wherein said bellows member is collapsible and expansible in response to volumetric variations in said fluid.

18. An ultrasound probe as recited in claim 17, wherein said case further has a proximal chamber located adjacent to and sealably separated from said enclosed volume, and wherein said open end of said bellows member is in open communication with said proximal chamber for internal pressure equalization therebetween.

19. An ultrasound probe as recited in claim 18, wherein said case comprises:
   a first portion defining said enclosed volume; and,
   a second portion selectively disconnectable from and connectable to said first portion to define said proximal chamber.

20. An ultrasound probe as recited in claim 17, wherein at least said closed end portion of said bellows member is elastically deformable.

21. An ultrasound probe as recited in claim 20, wherein said closed end portion of said bellows member is elastically expandable in response to volumetric variations in said fluid.

22. An external ultrasound probe comprising:
   a case having an enclosed volume;
   a fluid disposed within said enclosed volume;
   a bubble-trap member fixedly positioned relative to said case within said enclosed volume and having a distal-facing, concave surface, said distal-facing concave surface of said bubble trap defining a recess, wherein a distal portion of said enclosed volume is defined distal to said bubble-trap member and a proximal portion of said enclosed volume is defined proximal to said bubble-trap member, and wherein an aperture is provided through said bubble-trap member to fluidly interconnect from said distal portion of said enclosed volume to said proximal portion of said enclosed volume;
   an ultrasound transducer array supportably interconnected to said bubble-trap member and immersed in said fluid, wherein said ultrasound transducer array and said bubble-trap member are each supportably cantilevered from an end of said case proximal to said bubble-trap member and said bubble trap member and said ultrasound transducer array are otherwise free from fixed engagement with said case;
   a motor at least partially disposed within said recess defined by said bubble-trap member within said enclosed volume, wherein said motor is operatively interconnected to said ultrasound transducer array to affect said reciprocal pivotal movement thereof; and
   a bellows member having a flexible, closed-end portion located in said fluid within said case and an open-end isolated from said fluid, wherein said bellows member is collapsible and expansible in response to volumetric variations in said fluid.

* * * * *